(12) United States Patent
Angermann et al.

(10) Patent No.: US 7,501,457 B2
(45) Date of Patent: Mar. 10, 2009

(54) DENTAL MATERIALS BASED ON MULTICYCLIC ALLYL SULPHIDES

(75) Inventors: Jörg Angermann, Sargans (CH); Peter Burtscher, Rankweil (AT); Urs Karl Fischer, Arbon (CH); Norbert Moszner, Triesen (LI); Volker M. Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 206 days.

(21) Appl. No.: 11/482,164

(22) Filed: Jul. 7, 2006

(65) Prior Publication Data

US 2007/0203256 A1 Aug. 30, 2007

(30) Foreign Application Priority Data

Feb. 24, 2006 (EP) .................. 06110429

(51) Int. Cl.
*A61K 6/083* (2006.01)
*C08F 28/06* (2006.01)
(52) U.S. Cl. .................. 523/116; 523/118; 526/256; 433/228.1; 540/59
(58) Field of Classification Search .................. 523/116, 523/118; 540/576; 526/256
See application file for complete search history.

(56) References Cited

U.S. PATENT DOCUMENTS 6,444,724 B1 * 9/2002 Stangel et al. ............... 523/116
6,566,413 B1 * 5/2003 Weinmann et al. ............ 522/71

FOREIGN PATENT DOCUMENTS

WO 2006/019471 6/1996

OTHER PUBLICATIONS

R. A. Evans et al., "Free Radical Ring-Opening Polymerization of Cyclic Allylic Sulfides: Liquid Monomers with Low Polymerization Volume Shrinkage", *J. Polym. Sci*: Part A Polym. Chem 39 (2001) pp. 202-215.
R. A. Evans et al., "Free-Radical Ring-Opening Polymerization of Cyclic Allylic Sulfies", *Macromolecules* 29 (1996), pp. 6983-6989.
R. A. Evans et al., "Free-Radical Ring-Opening Polymerization of Cyclic Allylic Sulfies. 2. Effect of Substituents on Seven- and Eight-Membered Ring Low Shrink Monomers", *Macromolecules* 33 (2002), pp. 6722-6731.
W. Weinmann et al., "Siloranes in dental composites", *Dent. Mat.* 21 (2005) pp. 68-74.

* cited by examiner

*Primary Examiner*—Tae H Yoon
(74) *Attorney, Agent, or Firm*—Nixon Peabody LLP

(57) ABSTRACT

Dental materials and associated methods are described based on multicyclic allyl sulphides with general Formula (I):

$$\left( \begin{array}{c} R^1 \\ \diagup \\ \diagdown \\ R^2 \end{array} \underset{S}{\overset{S}{\diagdown}} \underset{(CH_2)_m}{\diagup} R^5-X-R^3-Y \right)_n R^4$$

in which $R^1$ is H or a $C_1$-$C_{10}$ alkyl radical; $R^2$ is H or a $C_1$-$C_{10}$ alkyl radical; $R^3$ is absent or is a $C_1$-$C_{20}$ alkylene radical which can be interrupted by O or S, a cycloaliphatic $C_4$-$C_{12}$ radical, a bicyclic $C_6$-$C_{12}$ radical, a $C_6$-$C_{14}$ arylene or $C_7$-$C_{20}$ alkylene arylene radical; $R^4$ is an n-times substituted aliphatic $C_2$ to $C_{20}$ hydrocarbon radical which can be interrupted by O or S, a cycloaliphatic $C_4$-$C_{12}$ radical, an aromatic $C_6$-$C_{14}$ radical, an aliphatic-aromatic $C_7$-$C_{20}$ radical or a heterocyclic radical which can contain 4 to 20 carbon atoms and 1 to 6 heteroatoms which are selected from N, O, P and/or S atoms, or which is formed exclusively by these heteroatoms; $R^5$ is absent or is a $C_1$-$C_{10}$ alkylene radical; X is absent or is O, S, —O—CO— or —O—CO—NH—; Y is absent or is O, S, —O—CO— or —O—CO—NH—; m is 0 or 1 and n is an integer from 3 to 6.

16 Claims, No Drawings

DENTAL MATERIALS BASED ON MULTICYCLIC ALLYL SULPHIDES

The present invention claims priority pursuant to 35 U.S.C. §119 to European Patent Application No. EP 06110429.5 filed Feb. 24, 2006, the entire content of which is incorporated herein by reference.

FIELD OF THE INVENTION

The invention relates to dental materials based on radically polymerizable, multicyclic allyl sulphides. The dental materials according to the invention are particularly suitable as composites, cements, adhesives for the preparation of coatings or dental moldings.

BACKGROUND OF THE INVENTION

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art.

Radically polymerizable cyclic monomers are of particular interest due to their much lower polymerization shrinkage compared with linear monomers (cf. R. K. Sadhir, R. M. Luck, Expanding Monomers, CRC Press, Boca Raton etc. 1992).

WO 96/19471 discloses mono- or difunctional cyclic allyl sulphides which are said to be suitable for the preparation of adhesives, dental composites and optical lenses. These monomers are said to display a lower shrinkage during polymerization than conventional monomers. Unfortunately, compared with commercial dimethacrylates, these monomers are characterized by an unsatisfactory, too low reactivity during radical photopolymerization.

R. A. Evans, E. Rizzardo, Macromolecules 29 (1996) 6983-6989, describe the ring-opening polymerization of 6-methylene-1,3-dithiepane and 3-methylene-1,5-dithiacyclooctane. These monomers are said to be resistant to moisture and also acids and bases, but have a penetrating, unpleasant smell.

In later works, R. A. Evans, E. Rizzardo, Macromolecules 33 (2000) 6722-6731 and R. A. Evans, E. Rizzardo, J. Polym. Sci.: Part A Polym. Chem. 39 (2001) 202-215, the same authors investigate the influence of substituents on the polymerization of mono- and bicyclic allyl sulphides. In the case of unsymmetrically substituted monomers, amorphous polymerization products were obtained which are said to be characterized by a lower shrinkage compared with crystalline products. The investigated bicyclic monomer bis(6-methylene-1,4-dithiacycloheptane-2-ylmethyl)diglycolate produced a rubbery, soft polymer which is unsuitable for dental applications.

W. Weinmann, C. Thalacker, R. Guggenberger, Dent. Mat. 21 (2005) 68-74, describe dental materials based on cyclosiloxanes modified with cycloaliphatic epoxides, so-called siloranes, which are said to make possible a further reduction in the polymerization shrinkage. However, a disadvantage of these compounds is their sensitivity to acids.

SUMMARY OF THE INVENTION

According to certain aspects, the invention provides dental materials which display a reactivity comparable with materials based on dimethacrylates and low shrinkage during radical polymerization. Furthermore, the dental materials are intended to be acid-stable in order to be able to incorporate acid monomers and thus provide self-adhesive materials.

Dental materials according to the invention may contain at least one multicyclic allyl sulphide with general Formula (I)

Formula I

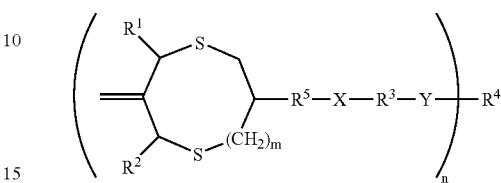

in which $R^1$ to $R^4$, X, Y, m and n, independently of one another, have the following meanings:

$R^1$=H or a $C_1$-$C_{10}$ alkyl radical,
$R^2$=H or a $C_1$-$C_{10}$ alkyl radical,
$R^3$=is absent or is a $C_1$-$C_{20}$ alkylene radical which can be interrupted by O or S, a cycloaliphatic $C_4$-$C_{12}$ radical, a bicyclic $C_6$-$C_{12}$ radical, a $C_6$-$C_{14}$ arylene or $C_7$-$C_{20}$ alkylene arylene radical,
$R^4$=an n-times substituted aliphatic $C_2$ to $C_{20}$ hydrocarbon radical which can be interrupted by O or S, a cycloaliphatic $C_4$-$C_{12}$ radical, an aromatic $C_6$-$C_{14}$ radical, an aliphatic-aromatic $C_7$-$C_{20}$ radical or a heterocyclic radical which can contain 4 to 20 carbon atoms and 1 to 6 heteroatoms which are selected from N, O, P and/or S atoms, or which is formed exclusively by these heteroatoms,
$R^5$=is absent or is a $C_1$-$C_{10}$ alkylene radical,
X=is absent or is O, S, —O—CO— or —O—CO—NH—,
Y=is absent or is O, S, —O—CO— or —O—CO—NH—,
m=0 or 1 and
n=an integer from 3 to 6.

DETAILED DESCRIPTION

Dental materials comprising a material according to Formula (I) defined above includes only compounds which conform to the chemical valence theory.

Alkyl and alkylene radicals can be branched or preferably straight-chained.

The radical $R^4$ is substituted n times by the molecule group in brackets.

The indication that groups can be interrupted by sulphur or oxygen atoms is to be understood to mean that the foreign atoms can be inserted into the carbon chain of the groups, i.e., are bonded on both sides by carbon atoms. The foreign atoms thus cannot occupy a terminal position. If several atoms are integrated into a carbon chain, they must in each case be separated from one another by at least one carbon atom. By "carbon chain" is meant straight and branched chains, but not rings. The total number of atoms integrated into the carbon chain is smaller by at least 1 than the number of carbon atoms in the chain.

The allyl sulphides of Formula (I) can be radically polymerized accompanied by ring opening. As the allyl sulphides used according to the invention have at least three polymerizable groups, i.e. allyl sulphide rings, they have cross-linking properties. The multicyclic allyl sulphides are also called multifunctional or n-functional allyl sulphides below. Unlike other ring-opening monomers, such as methylene-group-containing spiroorthocarbonates (SOC), spiroorthoesters (SOE), bicyclic orthoesters (BOE) or 1,1-disubstituted 2-vinylcyclopropanes (VCP), the cyclic allyl sulphides are characterized above all by a low moisture-sensitivity and a good radical copolymerization capacity with other vinyl monomers. In addition, they have a relatively high refractive index, which is advantageous for a dental application.

Dental materials are preferred which contain an allyl sulphide according to Formula (I) in which at least one and preferably all the variables have one of the following meanings:

$R^1$=H or methyl,
$R^2$=H or methyl,
$R^3$=is absent or is a $C_1$-$C_6$ alkylene radical, a cycloaliphatic $C_4$-$C_6$ radical or a $C_6$-$C_{12}$ arylene radical,
$R^4$=an n-times substituted aliphatic $C_2$- to $C_{10}$ radical, a cycloaliphatic $C_4$-$C_5$ radical, an aromatic $C_6$-$C_{12}$ radical, a heterocyclic $C_4$-$C_{12}$ radical which can contain 1 to 6 heteroatoms, the radical of a saturated or unsaturated phosphorus nitrogen compound such as e.g. a cyclic phosphazane or phosphazene radical,
$R^5$=is absent or a $C_1$-$C_3$ alkylene radical,
X=is absent or is O, —O—CO— or —O—CO—NH—,
Y=is absent or is O, —O—CO— or —O—CO—NH—,
m=0 or 1 and
n=3 or 4.

Dental materials are quite particularly preferred which contain an allyl sulphide according to Formula (I) in which at least one and preferably all the variables have one of the following meanings:

$R^1$=H or methyl,
$R^2$=H or methyl,
$R^3$=is absent or is a $C_1$-$C_6$ alkylene radical,
$R^4$=an n-times substituted aliphatic $C_2$ to $C_6$ radical, an aromatic $C_6$-$C_{10}$ radical, a cyanuric acid or preferably isocyanuric acid radical (symmetric or asymmetric hexamethylene diisocyanate trimer), a cyclic triphosphazene radical,
$R^5$=is absent,
X=O or —O—CO—NH—,
Y=is dispensed with or is O,
m=0 or 1 and
n=3 or 4.

A preferred phosphazane radical is the cyclotri(phosphazane) radical, a preferred phosphazene radical the cyclotri(phosphazene) radical.

The n-functional cyclic allyl sulphides of general Formula (I) can be obtained starting from suitably functionalized monocyclic allyl sulphides by known bond-linking reactions with correspondingly suitable n-functional precursor compounds. The monocyclic allyl sulphides, such as e.g. 6-methylene-1,4-dithiepanes (m=0) or 3-methylene-1,5-dithiacyclooctanes (m=1) can be prepared by etherification of suitable dihalogen compounds with dithiols, e.g. of 3-chloro-2-chloromethyl-1-propene with an ethane or propane dithiol derivative (HS—CH($R^5$—)—$CH_2$—SH or HS—$CH_2$—CH($R^5$—)—$CH_2$—SH) analogously to the literature (R. A. Evans, E. Rizzardo, J. Polym. Sci.: Part A Polym. Chem. 39 (2001) 202-215):

SPECIFIC EXAMPLE

On the other hand, e.g., 3-methylene-1,5-dithiacyclooctanes (m=1) functionalized with the group X' can also be synthesized by etherification of e.g. 1,3-dichloropropane Cl—$CH_2$—CH($R^5$—X')—$CH_2$—Cl functionalized with X' in the 2-position with 3-mercapto-2-mercaptomethyl-1-propene (HS—$CH_2$—C(=$CH_2$)—$CH_2$—SH) (analogous to DD 100 001).

SPECIFIC EXAMPLE

In the case of functionalized derivatives, a corresponding protective group technique must be used where necessary. Starting from the suitably functionalized monocyclic allyl sulphides, the n-functional cyclic allyl sulphides of general Formula I can then be prepared by known bond-linking reactions such as condensation (e.g. ether, ester or amide formation) or addition reactions (e.g. urethane formation) with correspondingly suitable n-functional precursor compounds:

SPECIFIC EXAMPLE FOR n=3
Preferred cyclic allyl sulphide monomers of Formula (I) are listed below:
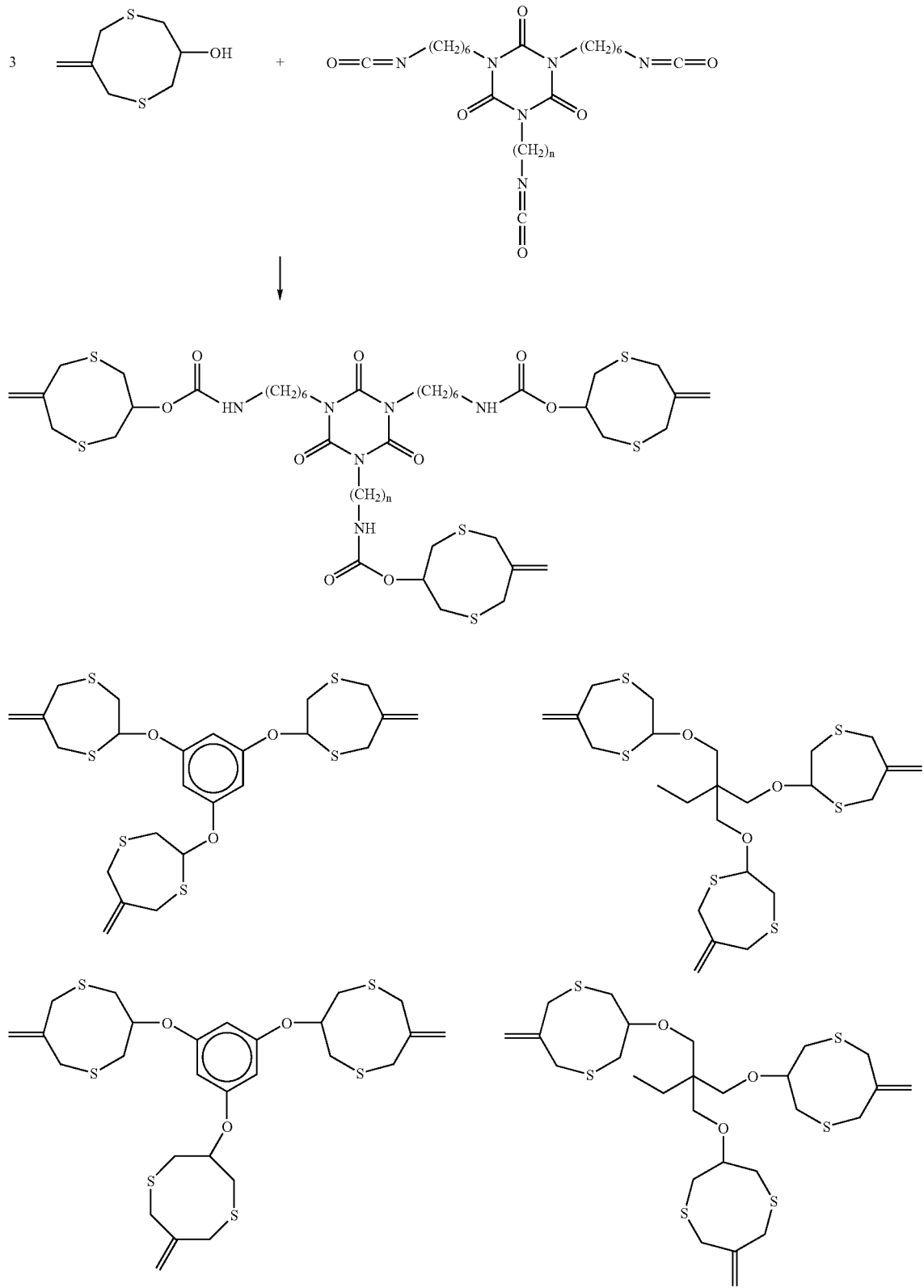

-continued
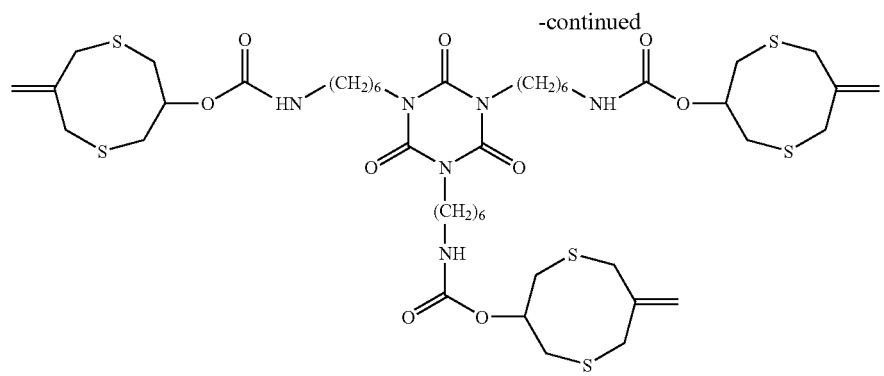
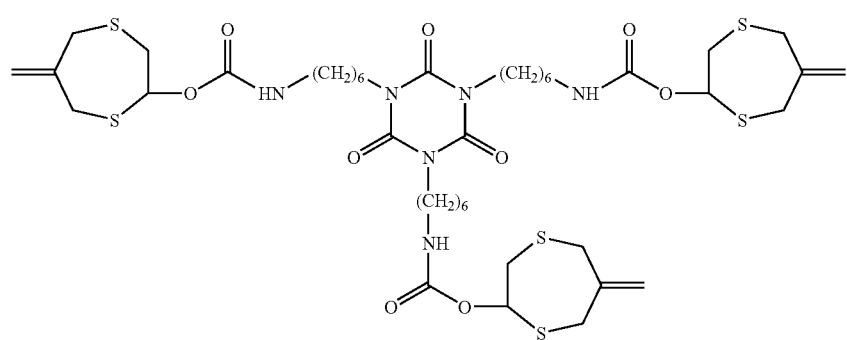
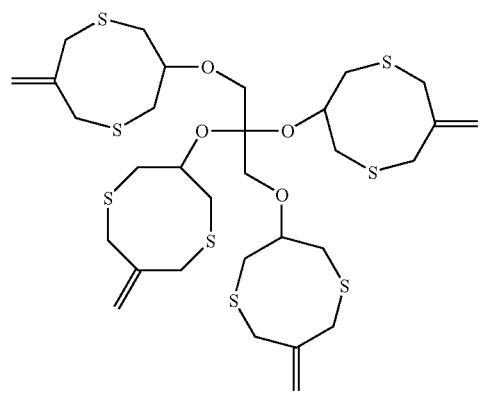
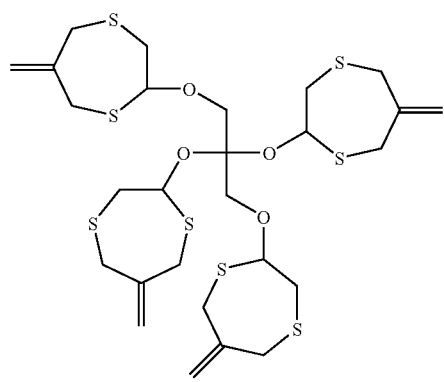
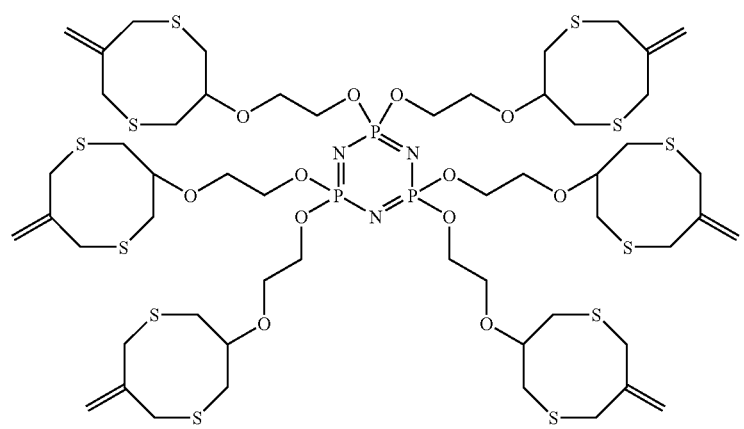

The dental materials according to the invention based on cyclic allyl sulphides of Formula (I) can be polymerized with the known radical initiators (cf. Encyclopedia of Polymer Science and Engineering, Vol. 13, Wiley-Intersci. Pub., New York etc. 1988, 754 et seq.) accompanied by ring-opening.

Photoinitiators (cf. J. P. Fouassier, J. F. Rabek (Eds.), Radiation Curing in Polymer Science and Technology, Vol. II, Elsevier Applied Science, London and New York 1993) are particularly suitable for the UV or visible region, such as benzoin ether, dialkylbenzil ketals, dialkoxyacetophenones, acyl- or bisacylphosphine oxides, α-diketones such as 9,10-phenanthraquinone, diacetyl, furil, anisil, 4,4'-dichlorobenzil and 4,4'-dialkoxybenzil and camphorquinone.

Furthermore, azo compounds such as 2,2'-azobis(isobutyronitrile) (AIBN) or azobis-(4-cyanovaleric acid), or peroxides such as dibenzoyl peroxide, dilauroyl peroxide, tert.-butylperoctoate, tert.-butylperbenzoate or di-(tert.-butyl)-peroxide can also be used. Benzopinacol and 2,2'-dialkylbenzopinacols are also particularly suitable as initiators for hot-curing.

To accelerate the initiation of peroxides or α-diketones, combinations with aromatic amines are preferably used. Preferred redox systems are: combinations of benzoyl peroxide, lauroyl peroxide or camphorquinone with amines such as in particular N,N-dimethyl-p-toluidine, N,N-dihydroxyethyl-p-toluidine, p-dimethylaminobenzoic acid ethyl ester or structurally related systems. In addition, redox systems which contain peroxides in combination with reduction agents, such as e.g. ascorbic acid, barbiturates or sulphinic acids, are also suitable.

The dental materials according to the invention can contain as polymerizable component exclusively cyclic allyl sulphides of Formula (I) or a mixture of same with conventional radically polymerizable monomers, in particular with monofunctional or multifunctional (meth)acrylates.

By monofunctional (meth)acrylic compounds are meant compounds with one, by multifunctional (meth)acrylic compounds compounds with two or more, preferably 2 to 3 (meth)acrylic groups. Multifunctional monomers have cross-linking properties.

Preferred monofunctional (meth)acrylates are commercially available monofunctional monomers such as methyl, ethyl, butyl, benzyl, furfuryl or phenyl(meth)acrylate and also 2-hydroxyethyl or propyl (meth)acrylate.

Particularly preferred are hydrolysis-stable monomers such as hydrolysis-stable mono(meth)acrylates, e.g. mesityl methacrylate or 2-(alkoxymethyl)acrylic acids, e.g. 2-(ethoxymethyl)acrylic acid, 2-(hydroxymethyl)acrylic acid, N-mono- or -disubstituted acrylamides, such as e.g. N-ethyl acrylamide, N,N-dimethacrylamide, N-(2-hydroxyethyl)acrylamide or N-methyl-N-(2-hydroxyethyl)acrylamide, and N-monosubstituted methacrylamides, such as e.g. N-ethyl methacrylamide or N-(2-hydroxyethyl)methacrylamide and in addition N-vinyl pyrrolidone and allyl ether. These monomers are liquid at room temperature and are therefore suitable as diluting agents.

Preferred multifunctional monomers are bisphenol-A-di(meth)acrylate, bis-GMA (an addition product of methacrylic acid and bisphenol-A-diglycidyl ether), UDMA (an addition product of 2-hydroxyethyl methacrylate and 2,2,4-trimethylhexamethylene diisocyanate), di-, tri- or tetraethylene glycol di(meth)acrylate, trimethylolpropane tri(meth)acrylate, pentaerythritol tetra(meth)acrylate, and also butanediol di(meth)acrylate, 1,10-decanediol di(meth)acrylate or 1,12-dodecanediol di(meth)acrylate.

Particularly preferred are hydrolysis-stable cross-linking monomers such as e.g. urethanes of 2-(hydroxymethyl) acrylic acid and diisocyanates such as 2,2,4-trimethylhexamethylene diisocyanate or isophorone diisocyanate, cross-linking pyrrolidones such as e.g. 1,6-bis(3-vinyl-2-pyrrolidonyl)-hexane, or commercially available bisacrylamides such as methylene or ethylene bisacrylamide, bis-(meth)acrylamides such as e.g. N,N'-diethyl-1,3-bis-(acrylamido)-propane, 1,3-bis-(methacrylamido)-propane, 1,4-bis-(acrylamido)-butane or 1,4-bis-(acryloyl)-piperazine, which can be synthesized from the corresponding diamines by reaction with (meth) acrylic acid chloride.

The dental materials according to the invention based on the cyclic allyl sulphides of Formula (I) are acid-stable and can therefore, according to a preferred embodiment, contain at least one radically polymerizable, acid-group-containing monomer which is capable of etching the tooth hard substance, with the result that a preconditioning of the tooth hard substance with acid is not necessary. Acid-group-containing monomers are also called acid monomers below. Such acid-group-containing monomers improve the adhesion of the materials to the tooth hard substance and thus provide low-shrinkage dental materials, such as e.g. filling composites or cements, with self-adhesive properties.

Preferred acid groups are carboxylic acid groups, phosphonic acid groups, phosphate groups and/or sulphonic acid groups, wherein groups with more than one acid hydrogen atom can be partly esterified. Particularly preferred are monomers with phosphonic acid groups or phosphate groups. The monomers can have one or more acid groups, compounds with 1 to 2 acid groups are preferred.

Preferred polymerizable carboxylic acids are maleic acid, acrylic acid, methacrylic acid, 2-(hydroxymethyl)acrylic acid, 4-(meth)acryloyloxyethyltrimellitic acid anhydride, 10-methacryloyloxydecylmalonic acid, N-(2-hydroxy-3-methacryloyloxypropyl)-N-phenylglycine and 4-vinylbenzoic acid.

Preferred phosphonic acid monomers are alkene phosphonic acids, vinyl phosphonic acid, 4-vinylphenyl phosphonic acid, 4-vinylbenzyl phosphonic acid, 2-methacryloyloxyethyl phosphonic acid, 2-methacrylamidoethyl phosphonic acid, 4-methacrylamido-4-methyl-pentyl phosphonic acid, 2-[4-(dihydroxyphosphoryl)-2-oxa-butyl]-acrylic acid and 2-[2-dihydroxyphosphoryl)-ethoxymethyl]-acrylic acid-2,4, 6-trimethyl-phenyl ester.

Preferred acid polymerizable phosphoric acid esters (phosphates) are 2-methacryloyloxypropyl mono- and dihydrogen phosphate, 2-methacryloyloxyethyl mono- and dihydrogen phosphate, 2-methacryloyloxyethyl-phenyl hydrogen phosphate, dipentaerythritol pentamethacryloyloxyphosphate, 10-methacryloyloxydecyl dihydrogen phosphate, dipentaerythritol pentamethacryloyloxyphosphate, phosphoric acid mono-(1-acryloyl-piperidine-4-yl)-ester, 6-(methacrylamido)hexyl dihydrogen phosphate and 1,3-bis-(N-acryloyl-N-propyl-amino)-propane-2-yl-dihydrogen phosphate.

Preferred polymerizable sulphonic acids are vinyl sulphonic acid, 4-vinylphenyl sulphonic acid or 3-(methacrylamido)propyl sulphonic acid.

To improve the mechanical properties or to set the viscosity, the dental materials can also contain organic or inorganic, particulate or fibrous fillers. Preferred inorganic particulate fillers are amorphous spherical materials, preferably with a primary particle size from 10 to 500 nm, based on oxides such as $ZrO_2$ and $TiO_2$ or mixed oxides of $SiO_2$, $ZrO_2$ and/or $TiO_2$, nanoparticulate (primary particle size from 10 to 100 nm) or microfine fillers (average particle size from 100 nm to 5 μm), such as pyrogenic silica or precipitated silica, and also minifillers such as quartz, glass ceramic or glass powder, preferably with an average particle size from 0.1 to 10 μm, and also X-ray-opaque fillers such as ytterbium trifluoride, preferably with an average particle size of approximately 200 nm, or nanoparticulate tantalum(V) oxide or barium sulphate, preferably with a primary particle size from 10 to 100 nm. In addition, glass fibres, polyamide or carbon fibres can also be used.

In addition, the dental materials according to the invention can contain one or more further additives such as stabilizers, UV absorbers, dyes, pigments and/or lubricants. In the case of adhesives, solvents such as ethanol, acetone or their mixtures with water can also be used.

The cyclic allyl sulphides of Formula (I) are particularly suitable for the preparation of dental filling composites, fixing cements, adhesives, coating materials and moldings. They are also suitable for the preparation of materials for inlays/onlays, artificial teeth and veneering materials for crowns and bridges.

A further subject of the invention is a process for the preparation of cured moldings. For this, a dental material according to the invention is formed into a molding, preferably a crown, bridge, an inlay or onlay, an artificial tooth or other dental restoration and then at least partially cured. The molding takes place in ways known per se.

The dental materials according to the invention are characterized by a low polymerization shrinkage, very good mechanical properties and, when using acid-group-containing monomers, by a high inherent adhesion to the tooth hard substance.

The dental materials according to the invention preferably contain:

| | |
|---|---|
| 1 to 95 wt.-% | allyl sulphide according to Formula (I); |
| 0.01 to 5 wt.-% | initiator for the radical polymerization; |
| 0 to 60 wt.-% | further radically polymerizable monomer; |
| 0 to 20 wt.-% | acid-group-containing monomer; |
| 0 to 85 wt.-% | filler. |

Unless otherwise stated, all wt.-percentages relate to the overall mass of the material. The further radically polymerizable monomers do not include the acid-group-containing monomers.

The exact composition is geared to the desired purpose. Dental materials for use as filling composites preferably contain:

1 to 45 wt.-%, particularly preferably 10 to 30 wt.-%, cyclic allyl sulphide according to Formula (I), 0.01 to 5 wt.-%, particularly preferably 0.1 to 2.0 wt.-%, initiator for the radical polymerization, 0 to 50 wt.-%, particularly preferably 0 to 10 wt.-%, additional radically polymerizable monomer, 30 to 85 wt.-%, particularly preferably 40 to 80 wt.-%, filler, 0 to 10 wt.-% acid-group-containing monomer.

Dental materials for use as cements preferably contain:

1 to 60 wt.-%, particularly preferably 20 to 50 wt.-%, cyclic allyl sulphide of Formula (I), 0.01 to 5 wt.-%, particularly preferably 0.1 to 2.0 wt.-%, initiator for the radical polymerization, 0 to 60 wt.-%, particularly preferably 0 to 20 wt.-%, additional radically polymerizable monomer, 20 to 60 wt.-%, particularly preferably 30 to 60 wt.-%, filler, 0 to 15 wt.-% acid-group-containing monomer.

Dental materials for use as coating materials preferably contain:

1 to 95 wt.-%, particularly preferably 10 to 60 wt.-%, cyclic allyl sulphide according to Formula (I), 0.01 to 5 wt.-%, particularly preferably 0.1 to 2.0 wt.-%, initiator for the radical polymerization, 0 to 60 wt.-%, particularly preferably 0 to 40 wt.-%, additional radically polymerizable monomer, 0 to 20 wt.-% filler, 0 to 10 wt.-% acid-group-containing monomer.

Dental materials for use as adhesives preferably contain:

1 to 80 wt.-%, particularly preferably 10 to 60 wt.-%, cyclic allyl sulphide according to Formula (I), 0.01 to 5 wt.-%, particularly preferably 0.1 to 2.0 wt.-%, initiator for the radical polymerization, 0 to 60 wt.-%, particularly preferably 0 to 40 wt.-%, additional radically polymerizable monomer, 0 to 40 wt.-%, particularly preferably 0 to 30 wt.-%, solvent, 0 to 20 wt.-% filler, 0 to 20 wt.-% acid-group-containing monomer.

The invention is described in further detail below with reference to the following non-limiting examples.

EXAMPLE 1

Synthesis of the Addition Product of the Trimer of Hexamethylene Diisocyanate with 7-hydroxy-3-methylene-1,5-dithiacylooctane (s-TDTO)

50.5 g (0.1 mol) symmetric hexamethylene diisocyanate trimer (Desmodur N 3300, Bayer AG; shear viscosity at 40° C.=4.3 Pas) was added dropwise at room temperature to a solution of 52.9 g (0.3 mol) 7-hydroxy-3-methylene-1,5-dithiacylooctane, which can be obtained by etherification of 2-hydroxy-1,3-dichloropropane with 3-mercapto-2-mercaptomethyl-1-propene, 12 mg TEMPO (2,2,6,6-tetramethyl-piperidine-1-oxyl, inhibitor), 25 mg MEHQ (hydroquinone monomethyl ether, stabilizer) and 0.2 g Metatin 812 (dibutyltin dioctoate, catalyst) in 100 ml methylene chloride. After 48 h stirring, no further isocyanate bands were detectable in the IR spectrum. The clear reaction mixture was washed twice with 100 ml 1.0 N NaOH and three times with 100 ml of saturated sodium chloride solution. The organic phase was then dried with sodium sulphate, stabilized with 20 mg MEHQ, and the solvent completely removed on the rotary evaporator accompanied by introduction of air. 95.5 g (yield: 92%) of a white solid of the trifunctional monomer s-TDTO was obtained with a melting point of 55.1° C. and the structure:

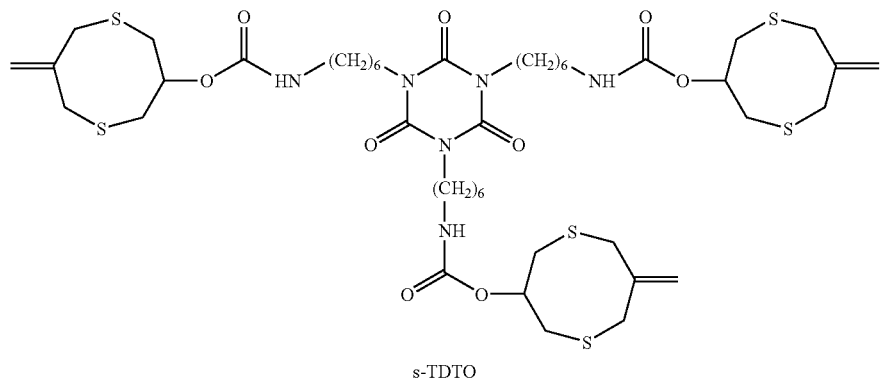

s-TDTO $^1$H-NMR (CDCl$_3$): 1.27 (m, 12H, CH$_2$), 1.48 (m, 6H, CH$_2$), 1.63 (br, 6H, CH$_2$), 3.02 (m, 12H, S—CH$_2$—CH—CH$_2$—S) 3.12 (m, 6H, CH$_2$N), 3.24 (m, 12H, =C$\overline{\text{H}_2}$S), 3.86 (t, $\overline{\text{6H}}$, CH$_2$N), 4.92 (br, m, 6H, CH and NH), 5.23 (s, 6H, =CH$_2$) ppm.

EXAMPLE 2

Synthesis of the Addition Product of the Asymmetric Trimer of Hexamethylene Diisocyanate with 7-hydroxy-3-methylene-1,5-dithiacylooctane (a-TDTO)

As in Example 1, 50.5 g (0.1 mol) of asymmetric hexamethylene diisocyanate trimer (Desmodur VP LS 2294, Bayer AG; shear viscosity at 40° C.=1.3 Pas) was reacted with 52.9 g (0.3 mol) 7-hydroxy-3-methylene-1,5-dithiacylooctane and worked up. 92 g (yield: 89%) of the trifunctional monomer a-TDTO was obtained as a colourless, highly viscous liquid with the following structure:

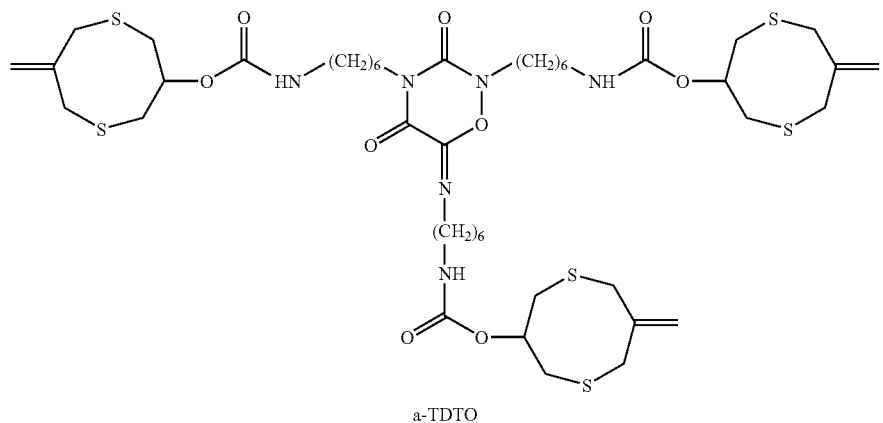

a-TDTO

EXAMPLE 3

Preparation of a Dental Cement Based on the Cyclic Allyl Sulphide from Example 2

According to Table 1 below, composite fixing cements based on (A) a conventional methacrylate mixture (comparison) and (B) the trifunctional cyclic allyl sulphide a-TDTO from Example 2 were prepared by means of a roll mill (Exakt type, Exakt Apparatebau, Norderstedt). Testpieces were prepared from the materials, which were irradiated twice for 3 minutes each time with a dental light source (Spectramat®, Ivoclar Vivadent AG) and thus cured. The bending strength, the bending E modulus and the exothermic time were determined according to the ISO standard ISO-4049 (Dentistry—Polymer-based filling, restorative and luting materials).

It can be seen from Table 2 that material B has mechanical properties which are comparable with those of material A based on a purely conventional methacrylate mixture, and that the reactivity of material B (exothermic time only 8 s) is even higher than that of the comparison material (exothermic time 13 s).

TABLE 1

Composition of the cements

| Constituent | Material A*) Proportions (wt.-%) | Material B Proportions (wt.-%) |
|---|---|---|
| Urethane dimethacrylate[1] | 31.6 | 31.6 |
| Decanediol dimethacrylate | 7.8 | — |
| a-TDTO (Ex. 2) | — | 7.8 |
| Aerosil OX-50 (Degussa) | 41.2 | 41.2 |
| Ytterbium trifluoride (Rhone-Poulenc) | 18.7 | 18.7 |
| Photoinitiator[2] | 0.7 | 0.7 |

*)Comparison material
[1]Urethane dimethacrylate from 2 mol 2-hydroxyethyl methacrylate and 1 mol 2,2,4-trimethylhexamethylene diisocyanate-1,6
[2]Mixture of camphorquinone (0.17%), p-N,N-dimethylaminobenzoic acid ethyl ester (0.30%), Lucirin TPO (0.23%, BASF)

TABLE 2

Material properties of the cements

| Material property | Material A*) | Material B |
|---|---|---|
| Bending strength (MPa) after 24 h | 120 | 120 |
| Bending strength (MPa) after 24 h WS[1] | 120 | 125 |
| Bending strength (MPa) after 7 d WS | 123 | 129 |
| Bending E modulus (GPa) after 24 h | 6.39 | 5.78 |
| Bending E modulus (GPa) after 24 h WS | 6.32 | 6.45 |
| Bending E modulus (GPa) after 7 d WS | 6.21 | 6.05 |
| Exothermic time (s) | 13 | 8 |

*)Comparison material
[1]WS = Water storage of the testpiece

EXAMPLE 4

Preparation of a Filling Composite Based on the Cyclic Allyl Sulphides from Example 2

According to Table 3 below, a filling composite was prepared based on a methacrylate mixture, incorporating the monomer a-TDTO from Example 2 by means of a laboratory kneader (type LPM 0.5 SP, Linden, Marienheide). Testpieces were prepared from the materials, which were irradiated twice for 3 minutes each time with a dental light source (Spectramat®, Ivoclar Vivadent AG) and thus cured. The bending strength, the bending E modulus and the polymerization shrinkage were determined according to the ISO standard ISO-4049 (Dentistry—Polymer-based filling, restorative and luting materials).

TABLE 3

Composition of the composite

| Constituent | Proportions (wt.-%) |
|---|---|
| a-TDTO (Ex. 2) | 19.74 |
| SR-348C (Satomer)[1] | 6.90 |
| Glass filler GM27884[2] | 72.00 |
| Photoinitiator[3] | 0.36 |

[1]Ethoxylated bisphenol-dimethacrylate which contains mainly 3 oxyethylene groups
[2]Barium aluminium silicate glass (Schott) silanized, average particle size 1.0 μm
[3]Mixture of camphorquinone (0.06%), p-N,N-dimethylaminobenzoic acid ethyl ester (0.12%), Lucirin TPO (0.08%, BASF) and diphenyliodonium hexafluorophosphate (0.10%)

TABLE 4

Material properties of the composite

| Material property | Measured value |
|---|---|
| Bending strength (MPa) after 24 h WS[1] | 131 |
| Bending E modulus (GPa) after 24 h WS[1] | 9.92 |
| Polymerization shrinkage (%) after 24 h | 1.71 |

[1]WS = Water storage of the testpieces at 37° C.

The example shows that filling composites with good mechanical properties can be obtained with the cyclic allyl sulphide a-TDTO from Example 2. The dilatrometrically ascertained polymerization shrinkage was only 1.7% compared with 2.7% for a comparison composite in which a pure dimethacrylate resin was used as matrix.

EXAMPLE 5

Preparation of a Filling Composite Based on the Cyclic Allyl Sulphide from Example 2 and the Acid Monomer MDP According to Table 5 below, a filling composite based on a methacrylate mixture was prepared, incorporating the monomer a-TDTO from Example 2 and the acid monomer MDP (=10-(methacryloyloxy)-decyldihydrogen phosphate) by means of a laboratory kneader (type LPM 0.5 SP, Linden, Marienheide).

TABLE 5

Composition of the composite

| Substances | Proportions (wt.-%) |
|---|---|
| a-TDTO (Ex. 2) | 17.34 |
| SR-348C (Satomer) | 5.70 |
| MDP | 3.60 |
| Glass filler GM27884[1] | 72.00 |
| Photoinitiator[2] | 0.36 |

[1]Barium aluminium silicate glass (Schott) silanized, average particle size 1.0 μm
[2]Mixture of camphorquinone (0.06%), p-N,N-dimethylaminobenzoic acid ethyl ester (0.12%), Lucirin TPO (0.08%, BASF) and diphenyliodonium hexafluorophosphate (0.10%)

The dentin adhesion of the composite was measured according to ISO/TS 11405 (Dental materials—Testing of adhesion to tooth structure). The procedure was as follows: the pulp and the root are removed from caries-free bovine teeth. The teeth are embedded in an epoxy resin and stored in water at 37° C. Before use, the teeth were polished with sandpaper (600 grid) until a level dentin surface becomes visible. This surface was washed with water and lightly dried. The embedded tooth was then fixed in a suitable holding device. A ring with an internal diameter of 4 mm and a height of 4 mm was secured to the tooth surface. The composite was packed into the ring in a layer thickness of approx. 2 mm and cured for 20 seconds with a dental lamp (Bluephase). A second layer of composite was applied over the first layer and likewise cured. The ring was removed and the tooth-composite combination stored in water at 37° C. After 24 hours, the polymerized composite was sheared off with an apparatus described in ISO/TS 11405. The expenditure of force required for this was divided by the cross-section surface of the testpiece, which produced a shear strength of 8.6 N/mm$^2$ for the tested composite. This dentin adhesion represents a very good value for a self-adhesive composite.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:

1. A dental material comprising at least one multicyclic allyl sulphide with general Formula (I):

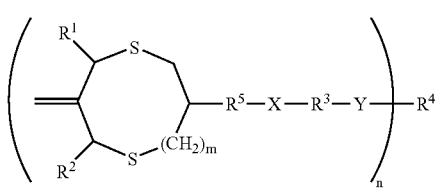

Formula I in which $R^1$ to $R^4$, X, Y, m and n, independently of one another, have the following meanings:

$R^1$=H or a $C_1$-$C_{10}$ alkyl radical;
$R^2$=H or a $C_1$-$C_{10}$ alkyl radical;
$R^3$=is absent or is a $C_1$-$C_{20}$ alkylene radical which can be interrupted by O or S, a cycloaliphatic $C_4$-$C_{12}$ radical, a bicyclic $C_6$-$C_{12}$ radical, a $C_6$-$C_{14}$ arylene or $C_7$-$C_{20}$ alkylene arylene radical;
$R^4$=an n-times substituted aliphatic $C_2$ to $C_{20}$ hydrocarbon radical which can be interrupted by O or S, a cycloaliphatic $C_4$-$C_{12}$ radical, an aromatic $C_6$-$C_{14}$ radical, an aliphatic-aromatic $C_7$-$C_{20}$ radical or a heterocyclic radical which can contain 4 to 20 carbon atoms and 1 to 6 heteroatoms which are selected from the group consisting of N, O, P, S, and a mixture thererof, or which is formed exclusively by these heteroatoms;
$R^5$=is absent or is a $C_1$-$C_{10}$ alkylene radical;
X=is absent or is O, S, —O—CO— or —O—CO—NH—;
Y=is absent or is O, S, —O—CO— or —O—CO—NH—;
m=0 or 1; and
n=an integer from 3 to 6.

2. The dental material according to claim 1, wherein at least one of the variables has one of the following meaning:
$R^1$=H or methyl;
$R^2$=H or methyl;
$R^3$=is absent or is a $C_1$-$C_6$ alkylene radical, a cycloaliphatic $C_4$-$C_6$ radical or a $C_6$-$C_{12}$ arylene radical;
$R^4$=an n-times substituted aliphatic $C_2$ to $C_{10}$ radical, a cycloaliphatic $C_4$-$C_5$ radical, an aromatic $C_6$-$C_{12}$ radical, a heterocyclic $C_4$-$C_{12}$ radical which can contain 1 to 6 heteroatoms, a saturated or unsaturated radical of a phosphorus nitrogen compound;
$R^5$=is absent or is a $C_1$-$C_3$ alkylene radical;
X=is absent or is O, —O—CO— or —O—CO—NH—;
Y=is absent or is O, —O—CO— or —O—CO—NH—;
m=0 or 1; or
n=3 or 4.

3. The dental material according to claim 2, in which at least one of the variables has the following meaning:
$R^1$=H or methyl;
$R^2$=H or methyl;
$R^3$=is absent or is a $C_1$-$C_6$ alkylene radical;
$R^4$=an n-times substituted aliphatic $C_2$ to $C_6$ radical, aromatic $C_6$-$C_{10}$ radical, a cyanuric acid or isocyanuric acid radical which can contain 1 to 6 heteroatoms, a cyclic triphosphazene radical;
$R^5$=is absent;
X=O or —O—CO—NH—;
Y=is absent or is O;
m=0 or 1; or
n=3 or 4.

4. The dental material according to claim 1, further comprising at least one initiator for the radical polymerization.

5. The dental material according to claim 1, further comprising at least one further radically polymerizable monomer.

6. The dental material according to claim 5, wherein the radically polymerizable monomer comprises 2 to 3 radically polymerizable groups.

7. The dental material according to claim 1, further comprising at least one acid-group-containing, radically polymerizable monomer.

8. The dental material according to claim 7, wherein the acid-group-containing monomer comprises a carboxylic acid group, phosphonic acid group, phosphate group sulphonic acid group or mixture thereof.

9. The dental material according to claim 1, which additionally contains at least one filler.

10. The dental material according to claim 1, comprising:

| | |
|---|---|
| 1 to 95 wt.-% | allyl sulphide according to Formula (I); |
| 0.01 to 5 wt.-% | initiator for the radical polymerization; |
| 0 to 60 wt.-% | further radically polymerizable monomer; |
| 0 to 20 wt.-% | acid-group-containing monomer; |
| 0 to 85 wt.-% | filler. |

11. A filling composite comprising the dental material of claim 1, the filling composite comprising:

| | |
|---|---|
| 1 to 45 wt.-% | allyl sulphide according to Formula (I); |
| 0.01 to 5 wt.-% | initiator for the radical polymerization; |
| 0 to 50 wt.-% | further radically polymerizable monomer; |
| 30 to 85 wt.-% | filler; and |
| 0 to 10 wt.-% | acid-group-containing monomer. |

12. A cement comprising the dental material of claim 1, the cement comprising:

| | |
|---|---|
| 1 to 60 wt.-% | allyl sulphide according to Formula (I); |
| 0.01 to 5 wt.-% | initiator for the radical polymerization; |
| 0 to 60 wt.-% | further radically polymerizable monomer; |
| 20 to 60 wt.-% | filler; and |
| 0 to 15 wt.-% | acid-group-containing monomer. |

13. A coating comprising the dental material of claim 1, the coating comprising:

| | |
|---|---|
| 1 to 95 wt.-% | allyl sulphide according to Formula (I); |
| 0.01 to 5 wt.-% | initiator for the radical polymerization; |
| 0 to 60 wt.-% | further radically polymerizable monomer; |
| 0 to 20 wt.-% | filler; and |
| 0 to 10 wt.-% | acid-group-containing monomer. |

14. An adhesive comprising the dental material of claim 1, the adhesive comprising:

| | |
|---|---|
| 1 to 80 wt.-% | allyl sulphide according to Formula (I); |
| 0.01 to 5 wt.-% | initiator for the radical polymerization; |
| 0 to 60 wt.-% | further radically polymerizable monomer; |
| 0 to 20 wt.-% | filler; |
| 0 to 20 wt.-% | acid-group-containing monomer; |
| 0 to 40 wt.-% | solvent. |

15. A method of preparing a dental restoration, the method comprising:

forming a molding comprising the dental material of claim 1, and at least partially curing the molding.

16. The method according to claim 15, wherein the molding is a crown, bridge, an inlay, onlay, an artificial tooth or another dental restoration.

\* \* \* \* \*